(12) United States Patent
Weber

(10) Patent No.: US 6,230,121 B1
(45) Date of Patent: May 8, 2001

(54) MEASUREMENT AND VALIDATION OF INTERACTION AND COMMUNICATION

(75) Inventor: Owen Wayne Weber, Coppell, TX (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/050,600

(22) Filed: Mar. 30, 1998

(51) Int. Cl.[7] .................................................. G08G 1/123
(52) U.S. Cl. .......................... 704/202; 455/456; 704/270
(58) Field of Search .................................. 704/270, 202; 455/456; 379/38, 106.2

(56) References Cited

U.S. PATENT DOCUMENTS

| | | | |
|---|---|---|---|
| 3,641,500 | * | 2/1972 | Greanias et al. ..................... 367/198 |
| 4,841,387 | * | 6/1989 | Rindfuss ............................. 360/72.1 |
| 5,170,164 | * | 12/1992 | Lewis .................................. 340/988 |
| 5,564,005 | * | 10/1996 | Weber et al. ........................ 704/278 |
| 5,592,607 | * | 1/1997 | Weber et al. ........................ 704/278 |
| 5,652,570 | * | 7/1997 | Lepkofker ............................ 379/38 |
| 5,712,619 | * | 1/1998 | Simkin ................................. 379/38 |
| 5,731,757 | * | 3/1998 | Layson, Jr. ........................... 379/38 |
| 5,889,474 | * | 3/1999 | LaDue ................................. 379/38 |

FOREIGN PATENT DOCUMENTS

| | | |
|---|---|---|
| 4-354485 | 12/1992 | (JP) . |
| 5-233992 | 9/1993 | (JP) . |
| 8-097927 | 4/1996 | (JP) . |

* cited by examiner

*Primary Examiner*—David Hudspeth
*Assistant Examiner*—Daniel Abebe
(74) *Attorney, Agent, or Firm*—Leslie A. VanLeeuwen; Felsman, Bradley, Vaden, Gunter & Dillon, LLP

(57) ABSTRACT

A method of monitoring an individual's interactions, by recording a value of an interaction parameter of the individual (such as conversational speech) using a measurement device, storing the value of the interaction parameter with an associated geographic coordinate, and generating a report, including the value of the interaction parameter and the associated geographic coordinate. The report can further include a timeframe associated with the particular value of the interaction parameter. The global positioning system (GPS) can be used to provide the geographic data. The directional orientation (attitude) of the individual may further be measured and used to facilitate selection of one or more other subjects as recipients of the communication (i.e., when the individual is facing one or more of the subjects). Analysis and report generation is accomplished at a remote facility which supports multiple measurement devices, so each device sends a unique identifier which distinguishes the particular measurement device.

26 Claims, 2 Drawing Sheets

Social Interaction for Device ID SI001, owner = John Doe.

Outgoing Communication

| Device ID | Owner | Date | Start Time | Elapsed Time | Words | Sentences |
|---|---|---|---|---|---|---|
| SI002 | Bill Jones | 10/5/97 | 8:36:04 AM | 00:01:12 | 27 | 3 |
| SI132 | Sue Smith | 10/5/97 | 10:31:37 AM | 00:27:01 | 1231 | 62 |
| Totals | | | | 00:28:13 | | |

Incoming Communication

| Device ID | Owner | Date | Start Time | Elapsed Time | Words | Sentences |
|---|---|---|---|---|---|---|
| SI002 | Bill Jones | 10/5/97 | 8:36:04 AM | 00:01:12 | 142 | 12 |
| SI132 | Sue Smith | 10/5/97 | 10:31:37 AM | 00:27:01 | 5519 | 368 |
| Totals | | | | 00:28:13 | | |

MEASUREMENT AND VALIDATION OF INTERACTION AND COMMUNICATION

BACKGROUND OF THE INVENTION

1. Field of the Invention

The present invention generally relates to electronic monitoring systems, and more particularly to a method and apparatus for measuring and validating social human interactions and communications, using computer and navigational technologies to remotely monitor group dynamics.

2. Description of Related Art

Social interaction and communication have always been important topics for study in the continuing pursuit of improving human existence. As technology evolves, it becomes increasingly important to understand how social intercourse is affected. New technologies not only add new stressors to human interaction, but further affect the quality and nature of these interactions as humans adjust their behaviors patterns to integrate technological advances.

Accordingly, the ability to monitor and measure human interaction and communication is quickly being recognized and promoted as an essential element of businesses, careers, and personal lives. Existing methods do not, however, provide an effective solution for such monitoring needs. Conventional monitoring systems are limited to those that provide details regarding an individual's separate existence, e.g., medical telemetry data, and do not relate to interactions with others. Navigational aids, such as those based on the global positioning system (GPS) or similar reckoning devices, can be used to track the movements of a vehicle or an individual, but do not yield any useful information regarding the individual's surroundings, other than that which can be inferred from the purely geographic information.

The following scenarios illustrate some simple examples wherein measurement tools might benefit various classes of individuals. A first example relates to polling validation. If an article in a periodical suggests that a primary factor in the breakdown of family values is that fathers do not spend enough time with their children then, to substantiate the claim, a poll may be taken, revealing that fathers spend only a certain amount of time each day with their children. A mechanism is needed to validate these findings, but none exists. To continue the foregoing example, a family counselor might want to know the actual amount of time a specific father spends with his children. Again, no reliable automated method exists for making such an accurate determination.

In another example, an employee may make a claim, during an employee evaluation, that she has been compelled to spend 50% of her time personally mentoring and counselling junior employees. The employee's manager needs a method to validate this claim, but no such method is available. A broader example relates to a psychologist's desire to determine a patient's source of stress. Due to busy lifestyles, the patient may be unable to isolate which social interaction is the cause of undue (serious) stress. There is, however, no conventional apparatus or technique that can be used to carry out this analysis (other than the very tedious and time-consuming approach of having someone review a series of video or audio recordings taken of the subject).

In light of the foregoing, it would be desirable to provide a method of monitoring an individual's interaction with the environment, such as by detecting or analyzing conversations. It would be further advantageous if the method were adapted to analyze interactions in a crowded, complex, and realistic environment, where it becomes more difficult to establish the identity of the intended recipient of any communication.

SUMMARY OF THE INVENTION

It is therefore one object of the present invention to provide a method and apparatus for monitoring social human interactions.

It is another object of the present invention to provide such a method which measures quantifiable social interaction parameters so as to validate observable behavior.

It is yet another object of the present invention to provide such a method which may be implemented in complex environments, and which further may be easily adapted to glean additional information from these more complex environments.

The foregoing objects are achieved in a method of monitoring an individual's interactions, generally comprising the steps of locating a measurement device proximate the individual, recording a value of an interaction parameter of the individual (such as conversational speech) using the measurement device, and storing the value of the interaction parameter with an associated geographic coordinate. A report can then be generated, including the value of the interaction parameter and the associated geographic coordinate. The report can further include a timeframe associated with the particular value of the interaction parameter. The global positioning system can be used to provide the geographic data. The directional orientation (attitude) of the individual may further be measured and stored with the value of the interaction parameter and the associated geographic coordinate. The attitude measurement can be used to facilitate selection of one or more other subjects as recipients of the communication (i.e., when the individual is facing one or more of the subjects). The analysis and report generation is preferably accomplished at a remote facility which supports multiple measurement devices, so each device sends a unique identifier which distinguishes the particular measurement device.

The above as well as additional objectives, features, and advantages of the present invention will become apparent in the following detailed written description.

BRIEF DESCRIPTION OF THE DRAWINGS

The novel features believed characteristic of the invention are set forth in the appended claims. The invention itself, however, as well as a preferred mode of use, further objectives, and advantages thereof, will best be understood by reference to the following detailed description of an illustrative embodiment when read in conjunction with the accompanying drawings, wherein:

DESCRIPTION OF AN ILLUSTRATIVE EMBODIMENT

Figure 1:
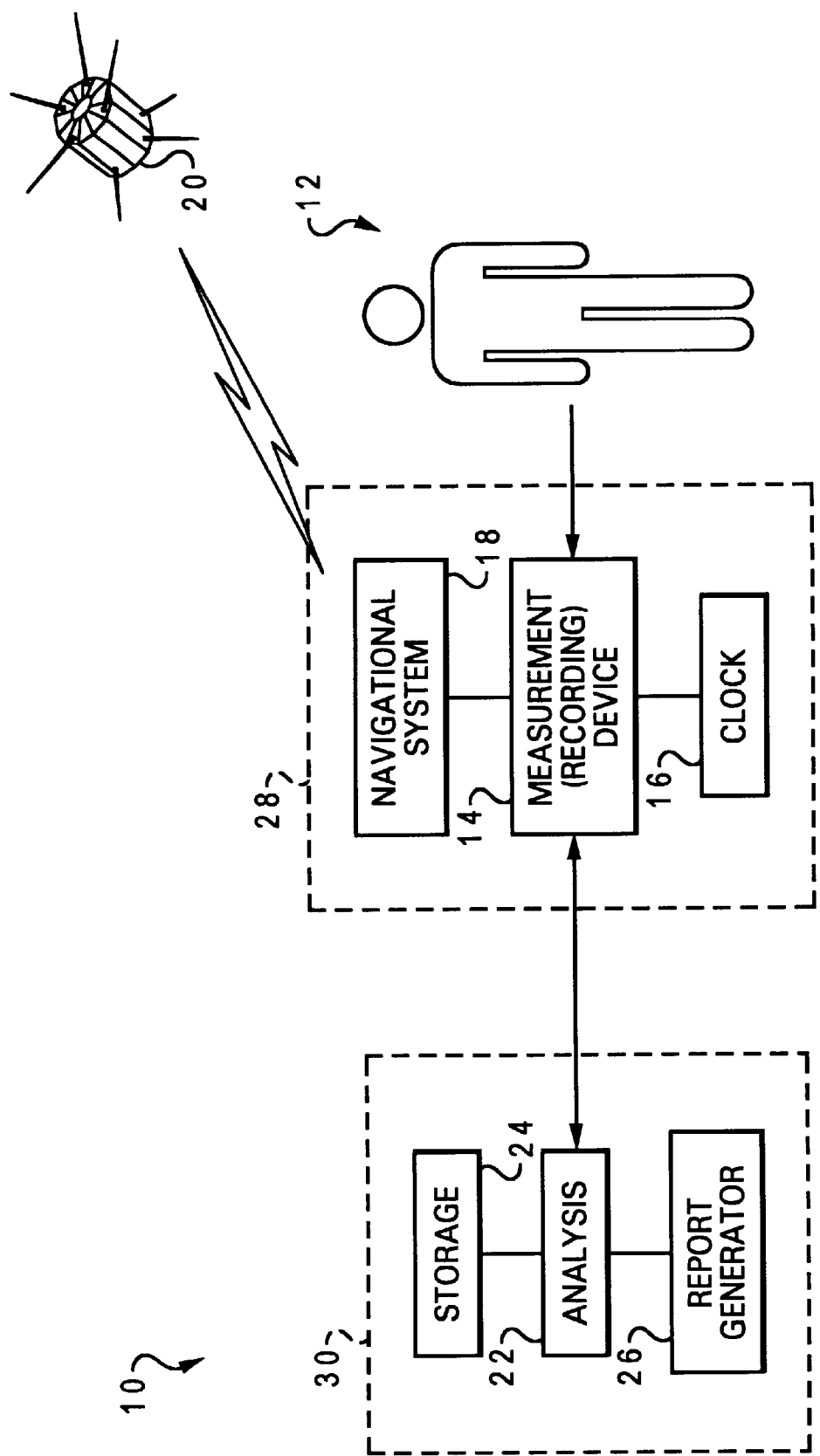
FIG. 1 is a block diagram of one embodiment of a social interaction monitoring system constructed in accordance with the present invention.

With reference now to the figures, and in particular with reference to FIG. 1, there is depicted a block diagram of one embodiment of a generalized monitoring system 10 constructed in accordance with the present invention, and adapted to measure and validate social human interaction and communication. System 10 is made available to one or more individuals 12 whose social interaction is to be monitored. System 10 includes a measurement device 14 that records (in a temporary storage device) social interaction parameters associated with the individual 12. These parameters may include any measurable phenomenon that is related to the interaction of an individual and his or her surroundings, such as audible signals associated with conversations (the speech of the owner of measurement device 14). A primary parameter may be word or syllable count, from which other variables (such as overall conversation times, or the number of conversations occurring during a day) may be inferred. In a more complicated embodiment utilizing voice-recognition equipment, the actual words which the individual has spoken could be recorded in sequence.

System 10 also includes a calendaring mechanism or clock 16 that allows measurement device 14 to record the timeframe(s) during which any words were spoken. In a preferred embodiment, a navigational system 18 is further used to provide geographic coordinates of the apparatus and, hence, of the owner, which information can again be recorded with the associated speech information. In this manner, it can later be determined whether a conversation took place at the owner's home, place of work, or some other location. Navigational system 18 can utilize global positioning system (GPS) technology which relies on earth-orbiting satellites 20 and a GPS receiver (located in navigational system 18). Other navigational aids besides GPS, however, can be used, such as a triangulation system using land-based antennas.

Information from measurement device 14 is transmitted to an analysis unit 22 which is used to organize the data according to whatever particular criteria are desired. If measurement device 14 is capable of more than one mode of operation (e.g., word count versus word recordation), analysis unit 22 may also be used to program measurement device 14, i.e., select a suitable mode based on the desired criteria. The information is preferably archived in a storage unit 24. The information is also processed by a report generator 26 which can prepare a report in any format compatible with the selected criteria.

As indicated by the dashed lines, system 10 may be physically separated into two subunits, including a local (sensing) unit 28, and a remote (computational) unit 30. These two units may communicate using conventional wireless communications equipment. In this manner, sensing unit 28, which is carried or worn by the individual under investigation, can be more lightweight and compact. Furthermore, a common computational unit 30 may be used for a plurality of sensing units 28. For example, computational unit 30 could be implemented as a computer system having a peripheral communications device which provides an interface to any sensing unit 28. Suitable software loaded on the computer allows a user to program the sensing units (if this feature is enabled), and to analyze downloaded data and generate reports. This feature includes the ability to share global parameters and stored data between similar devices. The use of a remote computational unit also reduces field operations since analysis of a number of sensing units can be performed at a centralized location. In this implementation, the information transmitted from sensing unit 12 includes a unique identifier which distinguishes that particular apparatus (individual).

Other features may be added to the basic construction shown in FIG. 1. The attitude (directional orientation) of an individual might be recorded in addition to other spatial parameters. Attitude information can be used to infer the subject of an individual's attention based on the direction he or she is facing during the social interaction. Thus, it might be determined that an individual was looking out a window while talking to himself, or that he was in bed (i.e., horizontally oriented) and was apparently talking during his sleep (perhaps further based on the time of night that the "conversation" took place).

These latter two examples point out that the present invention has applicability to investigating an individual's interaction with his or her surroundings even if no one else is present. The invention is particularly suited, however, to the further situation wherein the individual who is being monitored is actually having social interactions with other humans. Accordingly, in another variation of the invention, measurement device 14 is adapted to measure or store the speech of other owners of similar devices. This also may include the word counts, as well as the actual words spoken. For example, suppose that when John Doe first arrives at the office, he has a brief conversation with Bill Jones. Then later during the day, John has a meeting with Sue Smith. During these interactions, the social measurement devices worn by each subject will record the interactions. Furthermore, each device detects the presence and identity of the other subjects through wireless communication of device identifiers. The specific location of "other" subjects is detected and confirmed though GPS technology. At the end of the day, an example output report might be generated as shown in FIG. 2.

Figures 2, 3:
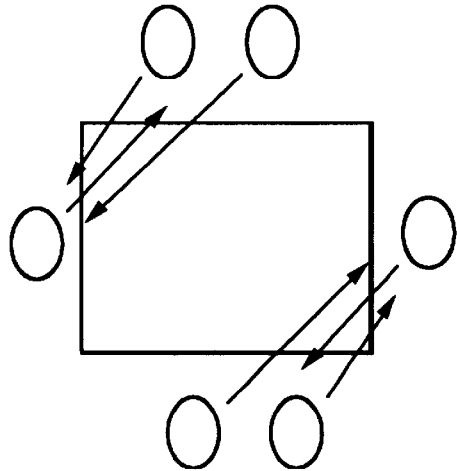
FIG. 2 is a pictorial representation of a report generated in accordance with the present invention, showing various interaction parameters between multiple subjects.
FIG. 3 is plan view of a group of people engaged in multiple conversations, illustrating how the directional orientation of the individuals can be used to determine which of them are intended as recipients of particular communications, in accordance with the present invention.

In FIG. 2, the "Outgoing Communication" table refers to the words spoken by the primary subject (John Doe) to the respectively noted other subjects, while the "Incoming Communication" table refers to the words spoken by those other subjects to the primary subject. In this embodiment, the analysis software includes the ability to determine an approximate sentence count, based on the number of successive exchanges between the individuals. Upon request, any or all of the actual conversations may also be reproduced. The user of system 10 (not usually the subject) may have the capability of tailoring the output of the report.

In a relatively crowded environment, it may be more difficult for the analysis unit to establish the identity of the intended recipient of any communication. To facilitate this determination, the invention may use the aforementioned attitude measurement to provide crowd reckoning. With further reference to FIG. 3, six people have just finished a meeting around a table, and have broken up into two separate conversations, with two people on one side of the table talking with the individual at the left head of the table, and the two people on the other side of the table talking with the individual at the right head of the table. The interaction devices (sensing units) can detect the intended recipient of a given communication according to the global attitudes of the subjects, i.e., the direction in which each is facing, relative to the others. For example, suppose that one subject speaks a sentence, but his interaction device detects that there are five possible recipients of the communication within range. The device then computes the global attitude of the speaker, communicates with the other five devices to acquire the global attitude of the other five owners, and decides which other person/persons are the intended recipients based on a geometric layout. This algorithm includes distance as well as global attitudes, along with preprogrammed user parameters to define the environment.

Thus, the device might deduce that the primary subject was speaking these words only to two of the other five subjects, since the other three subjects were not facing the primary subject. The physical device containing the necessary processing chips might be e.g., a necklace, an ankle bracelet, or an implant beneath the skin.

The present invention may be further modified to enhance the foregoing functionalities. The measurement device might include other sophisticated monitors, such as a blood pressure monitor (sphygmomanometer) to help determine which interactions cause more stress. The speech granularity can be specified, such as the aforementioned sentence detection, or elapsed times between statements, etc. The user may have the further capability of specifying the definition of the speech patterns, e.g., how to interpret incomplete sentences, poor grammar, etc. The user may also be provided with the capability of specifying rules for determining communications recipients, e.g., the closest person, the person the user is facing and/or the person who is facing the user, as well as a predetermined priority of known users. Moreover, a user may specify different ranges depending upon the environment, e.g., in a subject's office, no recipient will be more than 5 feet away, even if the device detects subjects farther away or, in a meeting room, any user within 40 feet might be a candidate for a recipient. For speeches to large crowds (formal speeches), additional parameters may be used to define the environment, such as a dialog mode versus a monologue mode, unlimited range, etc. Of course, languages other than English may be measured.

The described social interaction device can be built into telephone systems, as well as located on the person of the individual. With the former construction, phone communications can be tracked in addition to person-to-person communications. Similarly, the functionality can be built into computer systems, to track computer interactions.

Although the invention has been described with reference to specific embodiments, this description is not meant to be construed in a limiting sense. Various modifications of the disclosed embodiments, as well as alternative embodiments of the invention, will become apparent to persons skilled in the art upon reference to the description of the invention. For example, while the invention has been described with reference to audible conversations, it could also be applied to non-audible conversations (i.e., sign language, another form of speech), by monitoring hand activity in general, or specific hand movements. It is therefore contemplated that such modifications can be made without departing from the spirit or scope of the present invention as defined in the appended claims.

What is claimed is:

1. A method of monitoring an individual's interactions, comprising the steps of:

locating a measurement device proximate the individual;

recording a value of an interaction parameter of the individual, using the measurement device, wherein the interaction parameter pertains to a communication between the individual and one or more other subjects; and storing the value of the interaction parameter with an associated geographic coordinate.

2. The method of claim 1 wherein said storing step includes the step of determining the associated geographic coordinate using a global positioning system.

3. The method of claim 1 comprising the further step of generating a report including the value of the interaction parameter and the associated geographic coordinate.

4. The method of claim 1 wherein said storing step further stores the value of the interaction parameter with an associated timeframe.

5. The method of claim 4 comprising the further step of generating a report including the value of the interaction parameter, the associated geographic coordinate, and the associated timeframe.

6. The method of claim 1 further comprising the step of transmitting the value and the associated geographic coordinate with a unique identifier which distinguishes the measurement device, to an analysis unit.

7. The method of claim 6 wherein:

the analysis unit is remote from the measurement device; and said transmitting step uses wireless communications to transmit the value, the associated geographic coordinate, and the unique identifier to the analysis unit.

8. The method of claim 1 wherein:

said recording step further records a directional orientation of the individual; and said storing step further stores the directional orientation with the value of the interaction parameter and the associated geographic coordinate.

9. The method of claim 8 further comprising the steps of:

detecting the one or more other subjects using the measurement device; and selecting at least one of the other subjects as a recipient of the communication, based on a geometric layout which includes the directional orientation of the individual.

10. The method of claim 1 further comprising the step of detecting the one or more other subjects using the measurement device.

11. The method of claim 10 comprising the further step of generating a report including the value of the interaction parameter, the associated geographic coordinate, and another value of a related interaction parameter of at least one of the other subjects.

12. The method of claim 1 wherein said recording step includes the step of recording a speech parameter of the individual.

13. The method of claim 12 wherein said recording step counts the number of words spoken by the individual.

14. The method of claim 12 wherein said recording step records words which the individual has spoken.

15. A device for monitoring an individual's interactions, comprising:

means for measuring a value of an interaction parameter of an individual, wherein the interaction parameter pertains to a communication between the individual and one or more other subjects;

means for associating a geographic coordinate with the value of the interaction parameter; and means for generating a report including the value of the interaction parameter and the geographic coordinate.

16. The device of claim 15 wherein said associating means includes a global positioning system receiver.

17. The device of claim 15 further comprising means for associating a timeframe with the value of the interaction parameter, wherein said report further includes the associated timeframe.

18. The device of claim 15 further comprising:

means, remote from said measuring means, for analyzing the value and the associated geographic coordinate; and means for transmitting the value and the associated geographic coordinate to said analyzing means with a unique identifier which distinguishes said measuring means.

19. The device of claim 15 wherein:

said measuring means further records a directional orientation of the individual; and said associating means further associates the directional orientation of the individual with the value of the interaction parameter and the associated geographic coordinate.

20. The device of claim 19 further comprising:

means for detecting the one or more other subjects; and means for selecting at least one of the other subjects as a recipient of the communication, based on a geometric layout which includes the directional orientation of the individual.

21. The device of claim 15 wherein said generating means generates a report including the value of the interaction parameter, the associated geographic coordinate, and another value of a related interaction parameter of at least one of the other subjects.

22. The device of claim 15 wherein said measuring means includes means for recording a speech parameter of the individual.

23. The device of claim 22 wherein said recording means counts the number of words spoken by the individual.

24. The device of claim 22 wherein said recording means records words which the individual has spoken.

25. A method of monitoring an individual's interactions, comprising the steps of:

locating a measurement device proximate the individual;

recording a value of an interaction parameter of the individual, using the measurement device, wherein said recording step includes the step of recording a speech parameter of the individual and said recording step counts the number of words spoken by the individual; and storing the value of the interaction parameter with an associated geographic coordinate.

26. A device for monitoring an individual's interactions, comprising:

means for measuring a value of an interaction parameter of an individual and recording a speech parameter of the individual, wherein said recording means counts the number of words spoken by the individual;

means for associating a geographic coordinate with the value of the interaction parameter; and means for generating a report including the value of the interaction parameter and the geographic coordinate.

* * * * *